US009757269B2

(12) United States Patent
Strøbech et al.

(10) Patent No.: US 9,757,269 B2
(45) Date of Patent: Sep. 12, 2017

(54) OSTOMY BAG WITH OUTER ROTATABLE ADHESIVE FITTING WAFER

(75) Inventors: Esben Strøbech, Hoersholm (DK); Anders Bach, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 337 days.

(21) Appl. No.: 13/880,057

(22) PCT Filed: Oct. 20, 2011

(86) PCT No.: PCT/DK2011/050398
§ 371 (c)(1),
(2), (4) Date: Jun. 17, 2013

(87) PCT Pub. No.: WO2012/052032
PCT Pub. Date: Apr. 26, 2012

(65) Prior Publication Data
US 2013/0261576 A1   Oct. 3, 2013

(30) Foreign Application Priority Data

Oct. 20, 2010 (DK) ................................ 2010 70446

(51) Int. Cl.
A61F 5/448 (2006.01)
A61F 5/443 (2006.01)

(52) U.S. Cl.
CPC .............. A61F 5/448 (2013.01); A61F 5/443 (2013.01)

(58) Field of Classification Search
USPC ....................................................... 604/342
See application file for complete search history.

(56) References Cited

U.S. PATENT DOCUMENTS

| 4,610,677 A | * | 9/1986 | Mohiuddin | A61F 5/448 604/339 |
| 4,648,875 A | * | 3/1987 | Ferguson | A61F 5/448 604/339 |
| 4,664,661 A | * | 5/1987 | Ferguson | A61F 5/448 604/342 |
| 4,685,990 A | * | 8/1987 | Ferguson | A61F 5/44 156/253 |
| 4,710,182 A | | 12/1987 | Bryson | |
| 4,826,496 A | * | 5/1989 | Ferguson | A61F 5/448 604/339 |
| 4,828,553 A | * | 5/1989 | Nielsen | A61F 5/448 604/339 |
| 4,865,594 A | * | 9/1989 | Thomas | A61F 5/4404 604/332 |

(Continued)

FOREIGN PATENT DOCUMENTS

EP        0276898 A2     8/1988
GB        2432120 A1     5/2007
WO    WO2007128320 A2 *  11/2007  .............. C08G 77/46

Primary Examiner — Tatyana Zalukaeva
Assistant Examiner — Guy K Townsend
(74) Attorney, Agent, or Firm — Coloplast Corp., Coloplast A/S; Nick Baumann

(57) ABSTRACT

Disclosed is an ostomy bag 1 having an outer rotatable adhesive fitting wafer 15 attached thereto. This offers a higher degree of customization to the user, as the user may cut the adhesive fitting wafer in such a way that it fits to the contour of the skin and the user may also rotate the ostomy bag relative to the wafer in order to achieve a desired orientation of the ostomy bag.

15 Claims, 1 Drawing Sheet

(56) References Cited

U.S. PATENT DOCUMENTS

| | | | | |
|---|---|---|---|---|
| 4,883,477 A | * | 11/1989 | Steer | A61F 5/448 604/339 |
| 5,013,307 A | * | 5/1991 | Broida | A61F 5/445 604/332 |
| 5,203,806 A | | 4/1993 | Broida | |
| 5,269,773 A | * | 12/1993 | Vidal | A61F 5/448 604/338 |
| 5,662,628 A | * | 9/1997 | Hollands | A61F 5/448 285/317 |
| 5,771,590 A | * | 6/1998 | Colacello | A61F 5/441 30/360 |
| 5,957,905 A | * | 9/1999 | Steer | A61F 5/448 604/338 |
| 6,485,476 B1 | * | 11/2002 | von Dyck | A61F 5/441 600/29 |
| 2002/0032417 A1 | * | 3/2002 | Holtermann | A61F 5/448 604/338 |
| 2003/0088219 A1 | * | 5/2003 | Metz | A61F 5/448 604/339 |
| 2005/0143696 A1 | * | 6/2005 | Pedersen | A61F 5/448 604/332 |
| 2013/0261576 A1 | * | 10/2013 | Strobech | A61F 5/448 604/342 |

\* cited by examiner

OSTOMY BAG WITH OUTER ROTATABLE ADHESIVE FITTING WAFER

TECHNICAL FIELD

The following relates to an ostomy bag having an outer rotatable adhesive fitting wafer attached thereto. This offers a higher degree of customization to the user, as the user may cut the adhesive fitting wafer in a way that it fits to the contour of the skin and the user may also rotate the ostomy bag relative to the wafer in order to achieve a desired orientation of the ostomy bag.

BACKGROUND

One of the main concerns of ostomates using ostomy appliances having an adhesive base plate for attachment to the skin surrounding a stoma, and where an ostomy collecting pouch is attached to the base plate for collecting stoma output, is that the ostomy adhesive attachment may be comprised resulting in leakage or even detachment of the ostomy appliance.

Numerous attempts have been made to solve this problem and even though some attempts have been very successful, still there exist no products which completely solve this problem. Thus, there is a need to further develop and find improvements in order to solve this problem.

One reason why this is so difficult to solve is the fact that stomas and peoples anatomy are very different. Different considerations need to be made for thin people than for larger people, for different skin types, for placement of the stoma which may vary a lot from person to person, for scar tissue surrounding the stoma etc.

Thus, there exists a need to customize appliances to the personal user. However, allowing for too much customization will result in the fact that it takes long time for the user to prepare the ostomy appliance for use and also for many elderly or users having reduced motor skills too much customization is undesirable.

The following invention combines standard products with the option to customize parts of the ostomy appliance providing a higher degree of customization and thereby reducing the risk of leakage and detachment.

BRIEF DESCRIPTION

The present invention relates to an ostomy bag comprising a proximal wall facing the user during use and a distal wall facing away from the user during use, the proximal wall comprises an inlet opening through which output from a stoma is received during use, a connecting flange is attached to the proximal wall in an annular attachment area around the inlet opening and the connecting flange extends radially away from the annular attachment zone in at least in one area, wherein an adhesive fitting wafer is arranged around the attachment zone in such a way that it can be rotated relative to the connecting flange.

The adhesive fitting wafer provides an additional securing element, providing increased protection against leakage and detachment of the ostomy bag. At the same time the rotatable arrangement of the adhesive fitting wafer around the attachment zone allows for the user to align the adhesive fitting wafer along the skin surface for optimal fit. Such alignment may typically follow the contour of the skin such as folds. Moreover, users often have very personal desires to the orientation of the ostomy bag when applied. This may also be due to the contour of the skin surface, but may also be due to the position of the stoma and which type of clothing the specific user wears. Additionally, many users place the ostomy bag in a different orientation during night than during the day, since the user typically wants the bottom of the bag to point down in order for fecal matter to be collected properly. The rotatable arrangement of the adhesive fitting wafer allows for such customizable orientation of the ostomy bag between each use.

In one embodiment, the connecting flange may be an adhesive coupling wafer. This provides an ostomy bag that may be used in a two-piece ostomy appliance having adhesive connection between the base plate, which is attached to the skin, and the ostomy bag.

In an alternative embodiment, the adhesive coupling wafer is formed of a skin friendly adhesive for attachment to the skin surface. This provides a one-piece ostomy appliance, wherein adhesive coupling wafer functions as a base plate and may be attached directly to the skin. In other words, the adhesive coupling wafer functions as a base plate and is formed of a skin-friendly adhesive for attachment to the skin surface.

In another embodiment, a two-piece mechanical ostomy application may be provided by providing the connecting flange as a mechanical coupling flange for coupling with a complementary mechanical coupling flange arranged on an ostomy device base plate.

In one embodiment, a first through-going hole may be arranged in the adhesive fitting wafer and the radius of the through-going hole is larger than the radius of the attachment zone, but smaller than the radius of the at least one area of the connecting flange extending radially away from the annular attachment zone. This provides a particular advantageous arrangement of the adhesive fitting wafer on the ostomy bag, where the adhesive fitting wafer is securely coupled to the ostomy bag while at the same time being easy to rotate.

In one embodiment, the adhesive fitting wafer is formed as a thin sheet comprising a backing layer whereon a high tack adhesive is disposed. This provides a flexible adhesive fitting wafer which easily conforms to the contour of the skin surface and provides a secure attachment. Such high tack adhesives may include, but are not limited to, acrylate based adhesives or adhesives of the kinds disclosed in WO2007/128320.

In one advantageous embodiment, the adhesive fitting wafer is rectangular and has a width of at least three times the diameter of the connecting flange and a height of at least twice the diameter of the connecting flange. This provides an adhesive fitting wafer which has dimensions that are advantageous for a majority of skin contours and folds while at the same time it may be cut in order to for example avoid adhesion to some areas of the skin, which for example may be irritated.

Advantageously, a release liner may be provided on the adhesive side of the adhesive fitting wafer and wherein the release liner is split across the through-going hole. This provides a release liner which is easily removed before application of the adhesive fitting wafer.

DETAILED DESCRIPTION

Figure 1:
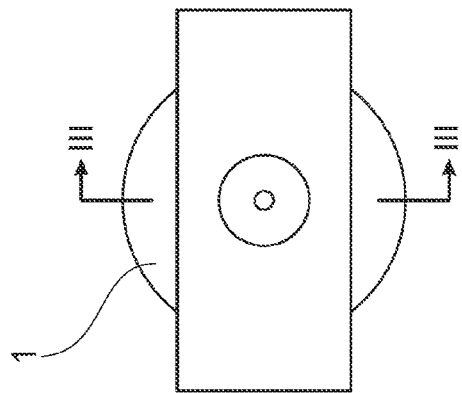
FIG. 1 shows an ostomy bag as described herein in an exploded view.
Figure 2:
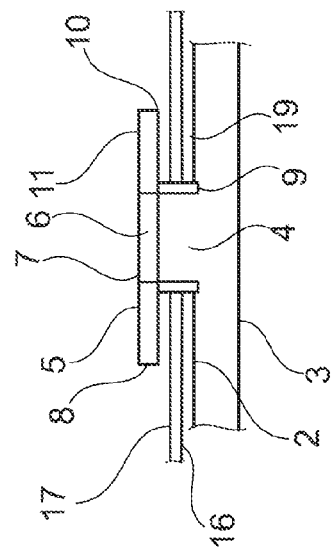
FIG. 2 shows an ostomy bag as described herein with the adhesive fitting wafer arranged around the ostomy bag.

An ostomy bag 1 is formed of a proximal sheet wall 2 and a distal sheet wall 3. The sheet walls are typically formed of two separate sheets which are welded together along their outer periphery. However, alternatively the ostomy bag may also be equipped with an outlet for emptying the stomal output collected in the bag at the convenience of the user.

The proximal sheet wall 2 is provided with an inlet opening 4 for receiving output from a stoma during use. An annular coupling wafer 5 is arranged on the proximal side of the proximal sheet wall 2. The coupling wafer is in the form of a disc having a central through-going hole 6 defining an inner periphery 7 of the coupling wafer. An outer periphery 8 defines the outer limit of the coupling wafer. The coupling wafer is attached to the proximal sheet wall around the inlet opening by an annular weld 9 provided at its inner periphery 7 in such a way that the inlet opening and the central through-going hole are co-axially arranged around a central axis A-A.

The coupling wafer is formed of a backing layer 10 of a material which is suitable for welding to the ostomy bag. Such materials are well known to the person skilled in the art. A skin friendly adhesive 11 is disposed on the proximal side of the backing layer. Such an adhesive may be a pressure sensitive adhesive (PSA) containing hydrocolloids. Such adhesives are well known and commonly used within ostomy appliances.

An adhesive fitting wafer 15 is arranged in rotational engagement with the ostomy bag and the coupling wafer allowing for relative rotational movement in respect to the ostomy bag and the coupling wafer around the axis A-A. The adhesive fitting wafer is formed of a wafer backing layer 16 whereon a skin friendly wafer adhesive 17 is disposed. The wafer adhesive may be of a kind which is thinner and more flexible than that of the adhesive of the coupling wafer. This allows the fitting wafer to better follow the contour of the body providing higher comfort and reducing the risk of detachment from the skin.

Figure 3:
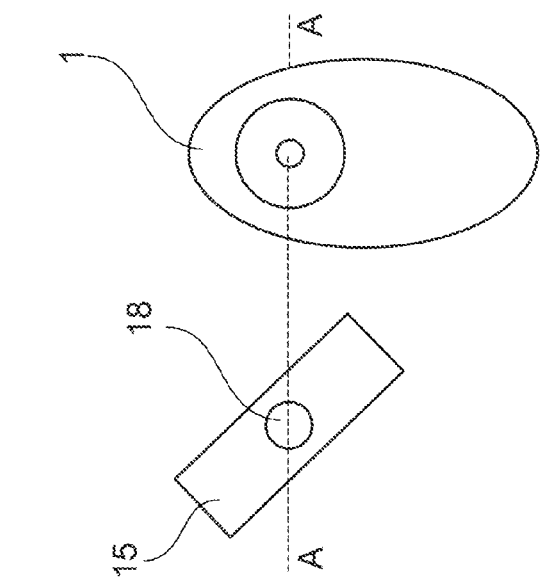
FIG. 3 shows in section the above along line III-III.

In order to couple the adhesive fitting wafer to the ostomy bag a through-going wafer hole 18 is formed in the adhesive fitting wafer. The wafer hole 18 has a diameter which is larger than the diameter of the annular weld 9, but smaller than the diameter of the outer periphery 8 of the coupling flange. Thus, the adhesive fitting wafer may be held in place in the recess 19 created between the coupling flange and the ostomy bag as shown in FIG. 3.

The invention claimed is:

1. An ostomy appliance comprising:
   an ostomy bag comprising a proximal wall facing a user during use and a distal wall facing away from the user during use, wherein the proximal wall comprises an inlet opening through which output from a stoma is received during use;
   a connecting flange comprising:
      an annular attachment area having a through-going hole connecting at a distal end to and around the inlet opening of the proximal wall; and
      a radial extension on a proximal end of the through-going hole of the annular attachment area; and
   an adhesive fitting wafer attached around the through-going hole of the annular attachment area between the distal end of the through-going hole and the proximal end of the through-going hole, the adhesive fitting wafer being positioned between and substantially parallel to each of the proximal wall and the radial extension of the connecting flange, wherein the adhesive fitting wafer is rotatable around the through-going hole of the annular attachment area in a direction substantially parallel relative to the connecting flange, wherein the adhesive fitting wafer includes a high tack adhesive disposed on substantially an entirety of a proximal side of the adhesive fitting wafer, with the high tack adhesive being configured to adhere and to conform the proximal surface of the adhesive fitting wafer to a contour of a skin surface of the user, and to adhere to substantially an entirety of a distal surface of the connecting flange around the proximal end of the through-going hole.

2. The ostomy appliance according to claim 1, wherein the connecting flange is an adhesive coupling wafer.

3. The ostomy appliance according to claim 2, wherein the adhesive coupling wafer is a base plate including the high tack adhesive on the proximal side of the radial extension for attachment to the skin surface.

4. The ostomy appliance according to claim 1, wherein the connecting flange is a mechanical coupling flange for coupling with a complementary mechanical coupling flange of an ostomy device base plate.

5. The ostomy appliance according to claim 1, wherein the adhesive fitting wafer is rectangular and has a width of at least three times a diameter of the radial extension of the connecting flange and a height of at least twice the diameter the radial extension of the connecting flange.

6. The ostomy appliance according to claim 1, further comprising a release liner covering the adhesive on the proximal side of the adhesive fitting wafer and wherein the release liner has a split formed in the release liner.

7. The ostomy appliance according to claim 1, wherein the adhesive fitting wafer is defined between an inner periphery located at the through-going hole of the annular attachment area and an outer periphery located at a distance from the inner periphery.

8. The ostomy appliance according to claim 1, wherein the high tack adhesive is configured to adhere to the radial extension of the connecting flange and to the skin surface of the user.

9. The ostomy appliance according to claim 1, further comprising an adhesive disposed on a proximal side of the radial extension of the connecting flange.

10. The ostomy appliance according to claim 1, wherein the high tack adhesive is configured to adhere to the radial extension of the connecting flange.

11. The ostomy appliance according to claim 1, wherein the adhesive fitting wafer is formed as a thin sheet.

12. The ostomy appliance according to claim 7, wherein the high tack adhesive extends between the inner periphery and the outer periphery of the adhesive fitting wafer.

13. The ostomy appliance according to claim 1, wherein the adhesive fitting wafer includes a backing layer with the high tack adhesive disposed on a side of the backing layer facing the connecting flange.

14. The ostomy appliance according to claim 1, wherein an external surface of the proximal side of the adhesive fitting wafer consists essentially of the high tack adhesive.

15. The ostomy appliance according to claim 1, wherein the proximal wall and the radial extension of the connecting flange form a recess therebetween with the adhesive fitting wafer being positioned within the recess between the proximal wall and the radial extension of the connecting flange.

* * * * *